(12) United States Patent
Markelov

(10) Patent No.: US 6,277,649 B1
(45) Date of Patent: Aug. 21, 2001

(54) RECIRCULATION ANALYSIS APPARATUS AND METHOD

(76) Inventor: Michael Markelov, 7276 Greenfield Trail, Chesterland, OH (US) 44026

( * ) Notice: Subject to any disclaimer, the term of this patent is extended or adjusted under 35 U.S.C. 154(b) by 0 days.

(21) Appl. No.: 09/365,520

(22) Filed: Aug. 2, 1999

Related U.S. Application Data

(60) Provisional application No. 60/096,112, filed on Aug. 10, 1998.

(51) Int. Cl.[7] ..................................................... G01N 1/22
(52) U.S. Cl. .............................. 436/181; 436/157; 422/98
(58) Field of Search ................................... 436/157, 181; 422/98

(56) References Cited

U.S. PATENT DOCUMENTS 5,441,700 * 8/1995 Markelov .............................. 422/83
5,693,538 * 12/1997 Capuano et al. ..................... 436/181

* cited by examiner

Primary Examiner—Jill Warden
Assistant Examiner—Monique T. Cole
(74) Attorney, Agent, or Firm—Ralph E. Jocke; Christopher L. Parmelee; Walker & Jocke

(57) ABSTRACT

A system for analysis of materials includes a sensor loop (100). The sensor loop includes sensors (130) therein. The sensor loop includes traps (120, 140). Sample material is desorbed from a first trap, moved past the sensors and collected in the second trap. The material is then desorbed from the second trap, moved past the sensors and again collected in the first trap. The amount and rate of flow of the sample material past the sensors is controlled, and the repeated exposure of the sensors to the sample material enhances sensitivity.

16 Claims, 3 Drawing Sheets

RECIRCULATION ANALYSIS APPARATUS AND METHOD

This Application claims benefit from Provisional Nos. 60/096,112, 09/365,520 filed Aug. 10, 1998.

TECHNICAL FIELD

This invention relates to analytical apparatus and methods. Particularly, this invention relates to a system which serves to pass sample vapors into operative relation with a sensor array of an analytical instrument.

BACKGROUND ART

Headspace technology is a relatively new technique which allows the sampling of the vapor of a material, so that the vapor may be analyzed using a gas chromatograph or other analytical instrument. The volatile (liquid or solid) material attains equilibrium with the vapor phase within a sealed vial. Equilibrium is established when the level of liquid or solid material in the vial no longer changes so that the total quantity of liquid or solid, and vapor remains constant. A syringe is then used to retrieve a small amount of vapor for analysis. Headspace technology is advantageous over conventional direct sample injection because it assures that only vapor enters the gas chromatograph. This is advantageous because it reduces the chance of contamination or destruction of the instrument due to introduction of unevaporated sample. Since the sample is in the vapor form, a larger sample size is possible. An increased sample size generally results in increased sensitivity.

The unique quality and character of many products are rooted in the chemical volatiles which comprise their odor. The ability to reliably measure and identify impurities, taints and adulteration is therefore valuable in many situations. Analytical techniques such as gas chromatography are sometimes used but data is often difficult to correlate with sensory information and is costly to produce. The Aromascan® technology produced by Aromascan Technologies allows odors to be measured electronically. Measurement of aromatic characteristics is very useful in certain applications.

A conventional Aromascan(& system is comprised of a sensory array and a gas sampling device that presents vapor of the sample material into connection with the array. The system is controlled and the data generated from array signals using an attached computer. The technology can recognize differences in the aroma, and hence the quality, of incoming raw materials. The ability to recognize or differentiate between a characterized product and an unknown imparts a wide range of potential applications for technology. The speed, sensitivity and accuracy of the technology translate into improved productivity and reduced costs.

Unfortunately, since this type of analysis is relatively new, there is still much needed improvement. Current Aromascan® sensors do not provide a means to control the rate of passage of sample materials before the sensor array. This lack of control translates into decreased sensitivity since the vapor for analysis travels too rapidly or slowly in front of the sensor array. An improper rate of travel in relation to the sensor array results in a lack of repeatability and potentially inaccurate results. Other types of analytical instruments may also benefit from better control of the flow of sample material thereto.

Thus, there exists a need for an apparatus and method to control the rate of travel of sample vapors in relation to a sensor array of an analytical instrument. There further exists a need for an apparatus which provides a controlled rate of flow of material collected from a sample into relation with the sensors of an analytical instrument.

DISCLOSURE OF INVENTION

It is an object of the present invention to provide a novel apparatus and method for passing headspace vapors in relation to a sensor array of an analytical instrument.

It is a further object of the present invention to provide a non-mechanical means of passing sample vapors in relation to a sensor array.

It is a further object of the present invention to provide an apparatus and method which improves sample data collection.

It is a further object of the present invention to provide an apparatus and method which improves accuracy of measurement.

It is a further object of the present invention to provide an apparatus and method which provides a controlled distribution of sample vapors.

It is a further object of the present invention to provide an apparatus which enables the sensor array to obtain a larger amount of data for a given amount of sample.

It is a further object of the present invention to provide a highly effective means for use with electronic aroma sensors.

It is a further object of the present invention to provide an apparatus which permits the passage of sample vapors past a sensor array multiple times.

It is a further object of the present invention to enable the process of thermal desorption of headspace vapors inside a chamber.

It is a further object of the present invention to provide a means for thermal desorption of headspace vapors between two traps located at opposite ends of a sample path.

The foregoing objects are accomplished in an exemplary apparatus and method which enables sample vapors to slowly pass a sensor of an analytical instrument, such as a sensor array of an electronic aroma sensor. The apparatus may include a gas sampling device. The gas sampling device extracts sample vapors from a vial containing a material to be analyzed and passes them into the apparatus. The apparatus further includes a purge gas source. The purge gas is preferably an inert gas such as helium. The purge gas may be used to move sample vapors in the system.

The apparatus further includes a valve mechanism which is in connection with a sensor loop. The pathways in the valve mechanism selectively direct the headspace vapors and the purge gas onto a first sample collection device which in the exemplary embodiment includes a first trap located at a first end of the sensor loop. The trap functions as a sample concentrator and consists of a collection vessel and a surrounding heater. Purge gas and other materials not collected in the first trap pass through the sample loop to a vent.

After the sample is collected in the first trap, the heater surrounding the first trap is turned on. Material in the sample thermally desorbs off the first trap and slowly travels through the sensor loop past the sensor mechanisms of the analytical instrument. The sensor mechanisms preferably include a sensor array of an electronic aroma sensor. The sensor array senses the material collected from the headspace and provides signals indicative of its chemical composition or other properties. After passing in front of the sensor array in the sensor loop, the sample material collects on a second sample collection device which in the exemplary embodiment includes a second trap located at the opposite end of the sensor loop from the first trap. The second trap again collects the sample material. The second trap includes a heater. When the heater is later turned on, the sample material thermally desorbs so that it may pass through the sensor loop in front of the sensor array again. The position of the valve mechanism is changed to enable reverse flow in the sensor loop. The first trap is cooled so that the material desorbed from the second trap is again collected in the first trap. The process is repeated until sample analysis is completed. Upon completion both traps may be heated. The sample vapors are vented to purge the sensor loop.

BEST MODES FOR CARRYING OUT INVENTION

Figure 1:
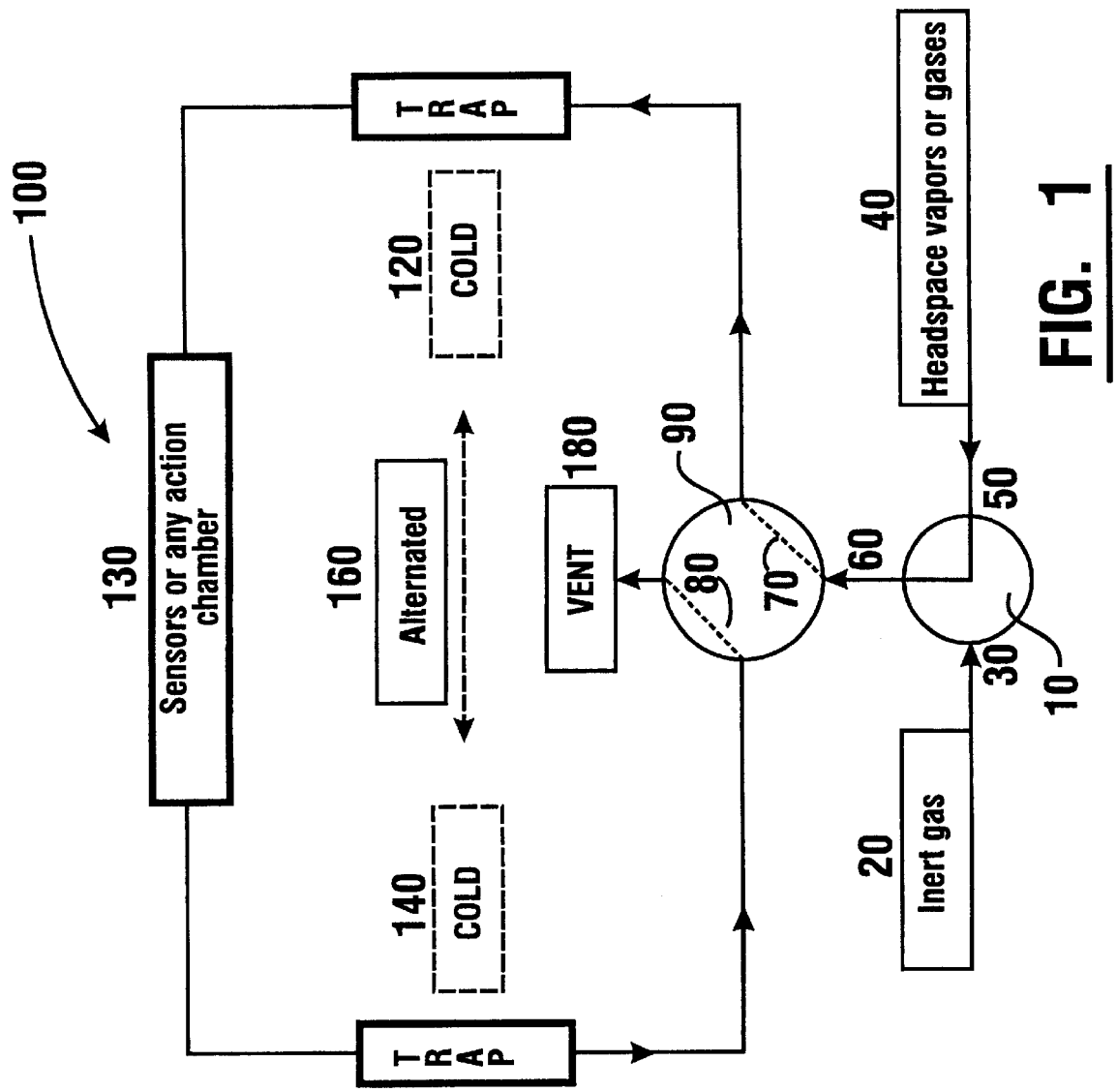
FIG. 1 is a schematic view of a recirculation analysis apparatus of an exemplary embodiment of the present invention in a first condition.

Referring now to the drawings and in particular to FIG. 1, there is shown therein a schematic view of an exemplary embodiment of the recirculation analysis apparatus of the present invention. The apparatus and its method of operation provide an improved technique for the analysis of chemical volatiles.

The apparatus includes a gas sampling device for collecting gaseous samples. In the exemplary embodiment the collection device collects a headspace sample. The sampling device collects sample material from a vial or a plurality of vials. Examples of devices and methods for collecting headspace samples are shown in allowed U.S. patent application Ser. No. 09/131,291 filed Aug. 10, 1998 the disclosure of which is incorporated by reference as if fully rewritten herein. Vapor samples collected from the vials may be passed directly to a valve 10. Alternatively sample material may be first collected in a trap associated with a headspace sampling device. The sample material may then later be desorbed from the trap and delivered to valve 10.

The headspace sampler, trap or other source is schematically represented 40 in FIG. 1. An inert gas from a purge gas source 20 is passed through a line 30 into a valve 10. Valve 10 may be arranged such that the purge gas source 20 moves the sample gas through the valve. Alternatively the sample source may be operatively connected with a separate source of purge gas.

From valve 10 the sample passes through a line 60 into a valve 90 which is connected to a sensor loop 100. The sample travels across a path 70 in the valve and is directed to a first trap 120. In this example first trap 120 is initially in a cool condition. The compounds or materials of interest in the analysis are collected on the cold first trap. Material not collected in trap 120 moves through the sensor loop 100 past one or more sensors 130. The material then moves through a second trap 140 in the sensor loop in this example. Second trap 140 is also maintained in a cool condition when a sample is introduced to the sensor loop. The remaining purge gas which passes through the second trap 140 passes to valve 90. The gas passes to a vent 120 or other outlet path through a path 80 in the valve.

Each of traps 120 and 140 is in operative connection with a heater. Heating the traps enables the material collected in the trap to be desorbed therefrom into the sensor loop 100. The heaters for the traps as well as valves 10 and 90 are preferably operated under the control of an electronic control system schematically indicated 160. The temperature to which a trap is heated can affect the desorption of particular compounds into the sample loop. In embodiments of the invention the temperature of the traps may be controlled to selectively analyze only certain compounds in the sample material.

Figure 2:
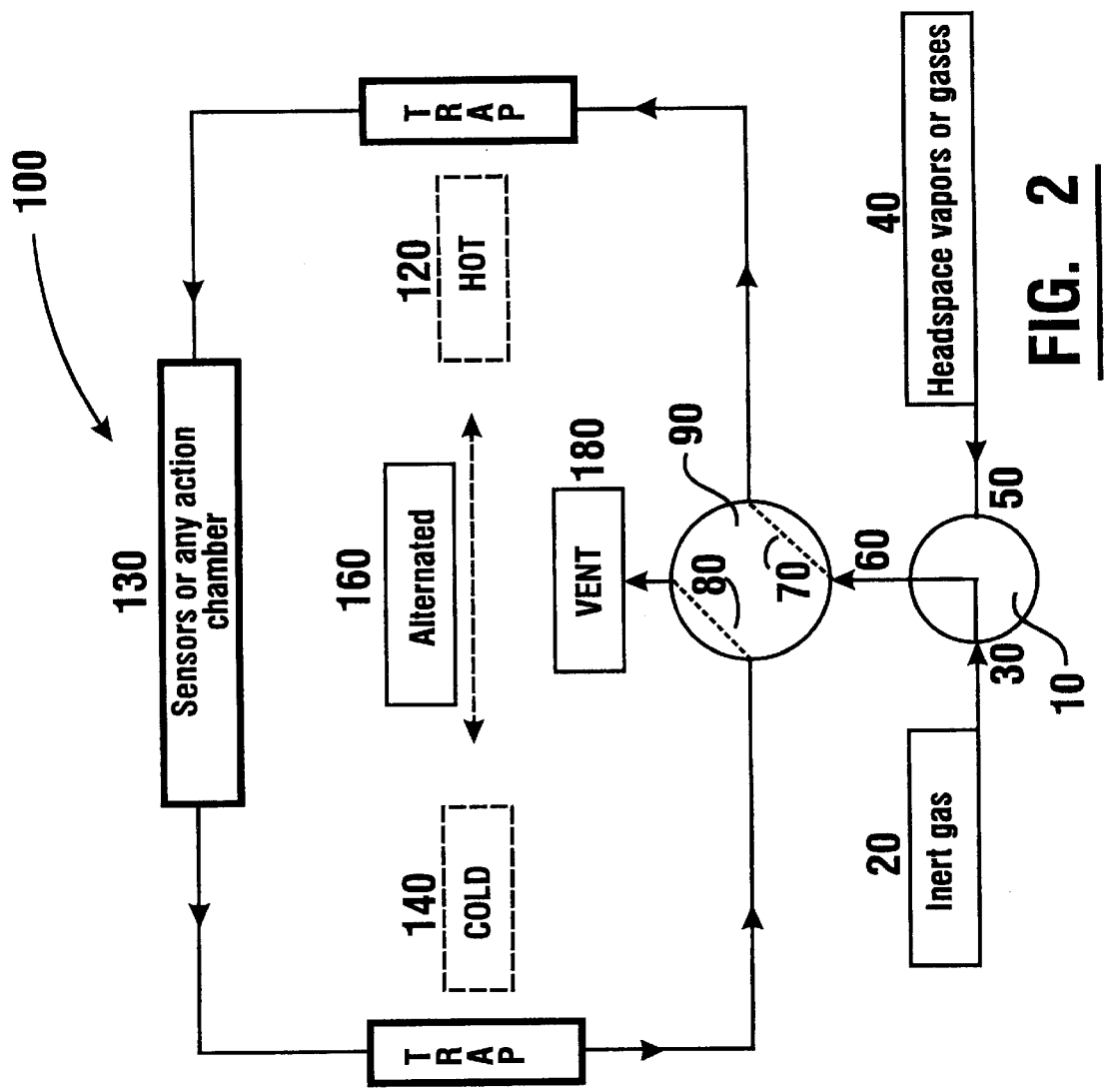
FIG. 2 is a schematic view of the apparatus in a second condition.

During analysis of the sample material the condition of valve 10 is changed from the condition represented in FIG. 1 to the condition schematically represented in FIG. 2. The heater in connection with first trap 120 is operated so that sample material is desorbed from the trap. The heating of the trap and the flow of purge gas from source 20 is preferably done at a controlled rate (in some cases with a zero or a near zero flow rate) to achieve flow at a desired rate through the sensor loop past the sensors 130. The rate of heating the trap 120 may also be controlled to regulate the rate of sample introduction. Controlling the temperature of the trap may also serve to liberate and discharge different substances from the trap at different times so that each substance liberated may be moved past the sensors with less additional substances in the sample flow. Of course the approach taken may be tailored to the particular analysis being conducted.

Sample material moved past sensors 130 in the sensor loop is collected in second trap 140. Trap 140 is maintained cold in the condition of the system shown in FIG. 2 to recapture the sample material liberated from trap 120. Material not captured in trap 140 passes out valve 90 to vent 180.

Figure 3:
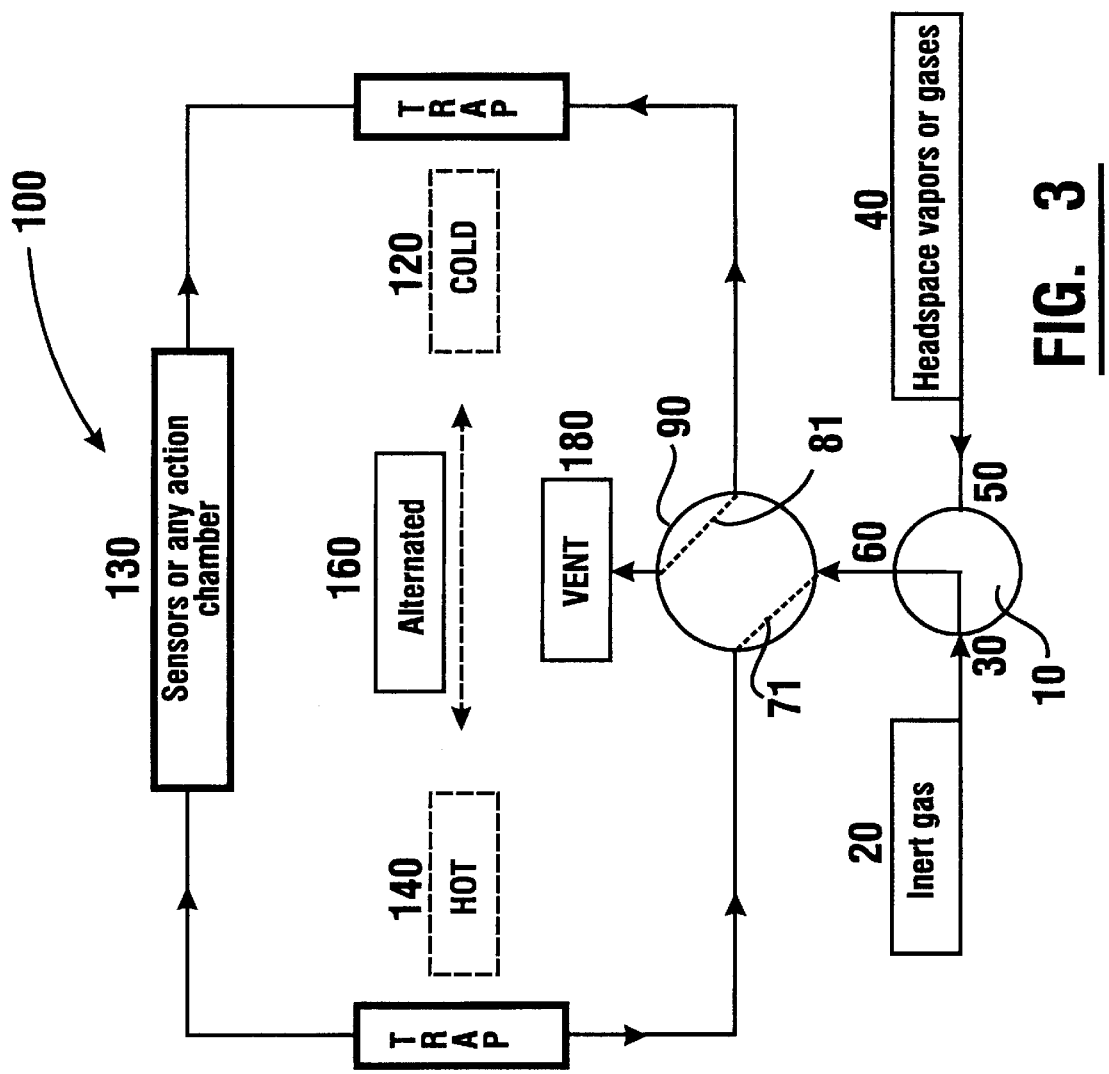
FIG. 3 is a schematic view of the apparatus in a third condition.

The sample material is again moved through the sensor loop 100 past sensors 130 by changing the condition of the valves and traps to the condition schematically shown in FIG. 3. In this condition purge gas passes through valve 10 and through a second path 71 in valve 90. Trap 140 is heated to liberate the sample material therein. The sample material is moved past the sensors 130 by convection and/or the controlled flow of purge gas. The sample material collects in trap 120 which is now cool. Material not collected in trap 120 is passed to vent 180 through a path 81 in valve 90.

In the exemplary embodiment the process is carried out and repeated under the control of a control system schematically represented 160, so that the sample material is repeatedly moved past the sensors 130. The rate of sample flow may be controlled by the rate of heating the trap discharging the sample therefrom and/or by the controlled rate of flow through the valve(s) or other flow control devices from purge gas source 20. The amount and timing of the heating of the traps may also control the times and amounts of sample material to which the sensors 130 are exposed. Control system 160 may include a computer which includes a processor and a memory, and appropriate interfaces for controlling the heaters, valves and other devices in the system. The control system of the exemplary embodiment controls the traps to collect and discharge sample material therefrom, as well as the conditions of valves for flowing sample material for analysis past the sensor, as well as to introduce and purge the sample material from the sample loop.

When it is desired to clear the sensor loop, control system 160 may heat both traps. The flow of inert gas then moves all sample material from the sensor loop. The sensor loop is then made ready for the introduction of a new sample. Alternatively, when traps may contain material harmful to the sensors, appropriate valves, vents and/or bypasses may be included for clearing material from the system without exposing the sensors to the material.

In one exemplary embodiment of the invention the sensors include a sensor array of Aromascan® sensors which comprise electronic aroma sensors which are also referred to as an electronic nose. The rate of flow of material across such sensors can be made sufficiently slow, and repeated exposure to the sample may be made to achieve improved sensitivity. Of course in other embodiments other types of sensors may be used. In alternative embodiments other types of sensing devices, sample collection devices for holding and discharging material, and system configurations may be used. Alternative types of sensors may include reaction type sensors or mechanisms, or devices that act with or upon the sample material to provide an indication of the constituents, quantities or properties of the sample material. Numerous alternatives may be devices by those having skill in the art from the teachings herein.

Thus, the apparatus and method of the present invention achieves the above stated objectives, eliminates difficulties encountered in the use of prior systems, solves problems and attains the desirable results described herein.

In the foregoing description certain terms have been used for brevity, clarity and understanding, however no unnecessary limitations are to be implied therefrom because such terms are for descriptive purposes and are intended to be broadly construed. Moreover, the descriptions and illustrations are by way of examples and the invention is not limited to the details shown and described.

In the following claims any feature described as a means for performing a function shall be construed as including any means known to those skilled in the art to be capable of performing the recited function, and not just the particular means shown or described as performing the function in the foregoing description, or mere equivalents thereof.

Having described the features, discoveries and principles of the invention, the manner in which it is constructed and operated, and the advantages and useful results attained; the new and useful structures, devices, elements, arrangements, parts, combinations, systems, equipment, operations and relationships are set forth in the appended claims.

I claim:

1. A method comprising the steps of:
   (a) collecting sample material in a first collection device;
   (b) discharging the sample material as a vapor from the first collection device in a sensor loop;
   (c) moving the sample material as a vapor in a first direction in the sensor loop past at least one analytical sensor;
   (d) detecting at least one constituent, quantity or property of the sample material a first time with the at least one sensor;
   (e) collecting the sample material that has moved in the first direction past the sensor in a second collection device;
   (f) discharging the sample material as a vapor from the second collection device in the sensor loop;
   (g) moving the sample material as a vapor in a second direction in the sensor loop past the at least one analytical sensor;
   (h) detecting the at least one constituent, quantity or property of the sample material a second time with the at least one sensor, wherein detecting is improved relative to the first time.

2. The method according to claim 1 and further comprising:
   repeating step (a) wherein the material moved past the sensor in step (g) is collected in the first collection device.

3. The method according to claim 2 and further comprising repeating steps (b) through (g) whereby the material is repeatedly moved past the sensor.

4. The method according to claim 1 and further comprising the steps of:
   (i) discharging material from both the first collection device and the second collection device; and
   (j) venting the material out of the sensor loop.

5. The method according to claim 1 and prior to step (a) comprising the step of extracting the sample material as a vapor from a headspace in a container holding a substance for analysis.

6. The method according to claim 1 wherein the sensor includes an electronic aroma sensor, and wherein in steps (c) and (g) the sample material includes a vapor that passes the electronic aroma sensor.

7. The method according to claim 1 wherein the first collection device includes a selectively heatable first trap and wherein the second collection device includes a selectively heatable second trap, and wherein step (b) includes heating the first trap, wherein the sample material is discharged as a vapor from the first trap, and step (f) includes heating the second trap wherein the sample material is discharged as a vapor from the second trap.

8. The method according to claim 7 wherein in step (c) the sample material moves by convection responsive to heating the first trap.

9. The method according to claim 7 wherein in step (g) the sample material moves by convection responsive to heating the second trap.

10. The method according to claim 1 wherein step (c) includes delivering an inert gas into the sensor loop, wherein the gas flows in the first direction in the sensor loop and moves the sample material therewith.

11. The method according to claim 1 wherein step (g) includes delivering an inert gas into the sensor loop, wherein the gas flows in the second direction in the sensor loop and moves the sample material therewith.

12. The method according to claim 7 wherein in step (b) the first trap is selectively heated to selectively discharge at least one constituent of the sample material therefrom.

13. The method according to claim 7 wherein in step (b) the first trap is selectively heated to control a rate of discharge of sample material therefrom.

14. The method according to claim 7 and further comprising the step of:
   (i) heating the first trap;
   (j) heating the second trap; and
   (k) venting the sample material from the sensor loop.

15. The method according to claim 14 wherein step (k) includes flowing an inert gas through the sensor loop.

16. An apparatus comprising:
   a sensor loop including a first sample collection device, a second sample collection device and at least one analytical sensor positioned in the sensor loop intermediate of the first sample collection device and second sample collection device;
   a controller in operative connection with the first sample collection device and the second sample collection device, wherein the controller controls the sample collection devices to discharge and collect a sample material, wherein the sample material move as a vapor of times past the sensor in alternating direction in the sensor loop.

* * * * *

UNITED STATES PATENT AND TRADEMARK OFFICE
CERTIFICATE OF CORRECTION

PATENT NO.  : 6,277,649 B1  
DATED       : August 21, 2001  
INVENTOR(S) : Michael Markelov Page 1 of 1

It is certified that error appears in the above-identified patent and that said Letters Patent is hereby corrected as shown below:

<u>Column 6,</u>  
Line 63, replace "move" with -- moves --  
Line 64, "of times" is deleted  
Line 64, "in alternating direction" is deleted Signed and Sealed this Twenty-sixth Day of February, 2002

*Attest:*

*Attesting Officer*

JAMES E. ROGAN  
*Director of the United States Patent and Trademark Office*